United States Patent
Kishiyama et al.

(10) Patent No.: US 7,410,726 B2
(45) Date of Patent: *Aug. 12, 2008

(54) ELECTRICAL BATTERY ASSEMBLY AND METHOD OF MANUFACTURE

(75) Inventors: Clay Kishiyama, Burbank, CA (US); Andrew Szyszkowski, Canyon Country, CA (US); Hisashi Tsukamoto, Saugus, CA (US)

(73) Assignee: Quallion LLC, Sylmar, CA (US)

( * ) Notice: Subject to any disclaimer, the term of this patent is extended or adjusted under 35 U.S.C. 154(b) by 135 days.

This patent is subject to a terminal disclaimer.

(21) Appl. No.: 11/475,649

(22) Filed: Jun. 27, 2006

(65) Prior Publication Data

US 2006/0246346 A1    Nov. 2, 2006

Related U.S. Application Data

(63) Continuation of application No. 10/223,039, filed on Aug. 15, 2002, now Pat. No. 7,070,881.

(60) Provisional application No. 60/347,940, filed on Oct. 18, 2001.

(51) Int. Cl.
  H01M 2/30    (2006.01)
  H01M 2/08    (2006.01)

(52) U.S. Cl. ............... 429/178; 429/185; 429/211; 29/623.2

(58) Field of Classification Search ............ 429/161, 429/178, 185, 211; 29/623.2
See application file for complete search history.

(56) References Cited

U.S. PATENT DOCUMENTS

| | | | |
|---|---|---|---|
| 3,245,837 A | 4/1966 | Ikeda et al. | |
| 3,416,964 A | 12/1968 | Michalko | |
| 4,053,692 A | 10/1977 | Dey | |
| 4,105,833 A | 8/1978 | Greatbatch et al. | |
| 4,452,869 A * | 6/1984 | DeMoully et al. | ........... 429/161 |
| 4,663,247 A | 5/1987 | Smilanich et al. | |
| 4,792,503 A | 12/1988 | Eppley | |
| 4,802,275 A | 2/1989 | Freluche | |
| 4,964,877 A | 10/1990 | Keister et al. | |
| 5,306,581 A | 4/1994 | Taylor et al. | |
| 5,474,859 A | 12/1995 | Takeuchi et al. | |
| 5,558,962 A | 9/1996 | Marincie et al. | |
| 5,811,206 A | 9/1998 | Sunderland et al. | |
| 5,821,011 A | 10/1998 | Taylor et al. | |
| 5,843,594 A | 12/1998 | Cheong et al. | |
| 5,888,667 A | 3/1999 | Cheong et al. | |
| 5,896,647 A | 4/1999 | Shkuratoff | |
| 5,900,333 A | 5/1999 | Lake | |
| 6,001,504 A | 12/1999 | Batson et al. | |

(Continued)

FOREIGN PATENT DOCUMENTS

EP    0 714 142 A1    5/1996

(Continued)

*Primary Examiner*—Stephen J. Kalafut
(74) *Attorney, Agent, or Firm*—Gavrilovich Dodd & Lindsey LLP

(57) ABSTRACT

The method includes filling a case through a fill-hole in a cover of a case. The case is configured to hold an electrode assembly having at least one positive electrode and at least one negative electrode. The method also includes plugging the fill-hole with a plug. The plug includes a terminal for the battery.

20 Claims, 15 Drawing Sheets

U.S. PATENT DOCUMENTS

| | | | |
|---|---|---|---|
| 6,004,692 | A | 12/1999 | Muffoletto et al. |
| 6,007,938 | A | 12/1999 | Blancheton |
| 6,013,113 | A | 1/2000 | Mika |
| 6,013,389 | A | 1/2000 | Nakamaru et al. |
| 6,071,557 | A | 6/2000 | Haraguchi et al. |
| 6,113,658 | A | 9/2000 | Lane |
| 6,132,898 | A | 10/2000 | Kawamura |
| 6,143,442 | A | 11/2000 | Takahashi et al. |
| 6,258,485 | B1 | 7/2001 | Kitoh |
| 6,316,140 | B1 | 11/2001 | Hatazawa et al. |
| 6,319,628 | B1 | 11/2001 | Zama |
| 6,319,631 | B1 | 11/2001 | Bay et al. |
| 6,346,346 | B1 | 2/2002 | Naskali |
| 6,348,282 | B1 | 2/2002 | Okochi et al. |
| 6,379,839 | B1 | 4/2002 | Inoue et al. |
| 6,379,840 | B2 | 4/2002 | Kitoh et al. |
| 6,432,574 | B1 * | 8/2002 | Suzuki et al. ............ 429/161 |
| 6,485,859 | B1 | 11/2002 | Szyszkowski |
| 6,761,996 | B1 | 7/2004 | Kim et al. |
| 7,070,881 | B2 * | 7/2006 | Kishiyama et al. .......... 429/161 |
| 2001/0004503 | A1 | 6/2001 | Kondo |
| 2001/0007729 | A1 | 7/2001 | Kitoh et al. |
| 2001/0008725 | A1 | 7/2001 | Howard |
| 2001/0053476 | A1 | 12/2001 | Ruth et al. |
| 2002/0004162 | A1 | 1/2002 | Satoh et al. |
| 2002/0006543 | A1 | 1/2002 | Sagawa et al. |
| 2002/0018940 | A1 | 2/2002 | Nirasawa et al. |
| 2002/0022174 | A1 | 2/2002 | Hallifax et al. |
| 2002/0022175 | A1 | 2/2002 | Hallifax et al. |
| 2002/0029464 | A1 | 3/2002 | Iijima et al. |
| 2002/0061438 | A1 | 5/2002 | Inoue et al. |

FOREIGN PATENT DOCUMENTS

| | | |
|---|---|---|
| JP | 04-002065 A2 | 1/1992 |
| JP | 2001185226 A2 | 7/2001 |

* cited by examiner

ELECTRICAL BATTERY ASSEMBLY AND METHOD OF MANUFACTURE

RELATED APPLICATIONS

This application is a continuation of U.S. patent application Ser. No. 10/223,039, filed on Aug. 15, 2002, entitled "Electric Battery Assembly and Method of Manufacture," now U.S. Pat. No. 7,070,881, which claims the benefit of U.S. Provisional Application 60/347,940 filed Oct. 18, 2001, each of which is incorporated herein in its entirety.

BACKGROUND OF THE INVENTION

The invention relates generally to an electrical storage battery, and more particularly to an assembly and a method of manufacture for an electrical storage battery expected to find use in conjunction with an implantable medical device, but which may also find use in other applications.

Electrical storage batteries are now in use in a wide range of applications. This range of applications is expected to increase in the future as storage battery technology continues to improve. As improved battery technology allows battery use in more, and more demanding, applications, the requirements imposed on the batteries' physical construction increases as well.

For example, new battery technologies have yielded small and lightweight batteries with long storage lives and high energy output capabilities. This has allowed the use of batteries in new applications such as permanently implantable medical devices including cardiac pacemakers and implantable cardiac defibrillators. Innovators will surely develop other battery-operated medical devices as medical practitioners' understanding of human anatomy and electrophysiology continues to improve.

Batteries for permanently implantable medical devices have very strict requirements. Such batteries should have very long useful lives, thereby allowing long periods between implantation and surgical replacement. The batteries should therefore be capable of high total power output, and have very low self-discharge rates.

Some devices require very high power output rates. For example, an implantable cardiac defibrillator must charge its capacitor and deliver an electrical charge to reestablish the normal rhythm of a beating human heart, preferably within a very few seconds. A battery for such a device must provide a very high energy-output rate to charge the capacitor as quickly as possible.

Batteries intended for permanent implantation in a human patient must be highly reliable over a long time. All internal components must be robust and reliable, and the connections between them stable and secure. Battery failure in an implantable medical device means surgical replacement in the best case. Battery failure at a critical moment can cause the patient's death.

An implantable device must be compatible with the patient's own internal body chemistry. In devices where the body or bodily fluids may contact the battery, the exterior of the battery must be of sufficiently biocompatible materials. The battery must include highly reliable sealing components, moreover, to isolate the components inside the battery and to insure that no battery electrolyte leaks out of the external case that encloses and contains the electrodes.

Some newer batteries include a remote recharging capability. These batteries can be recharged by a charging device disposed a short distance away from the battery. This is of course highly advantageous in an implantable medical device, because the battery can be recharged without invasive surgery to the patient's body.

It is advantageous for any battery, as with any manufactured article, for the manufacture and assembly to be made as simply, reliably, and cheaply as possible. The battery should include as few parts as are reasonably necessary, and those parts should be easy and quick to assemble.

There is a substantial and increasing need for new batteries, and for related manufacturing methods, that will provide batteries having long lives, high power output rates, and high total energy delivery. The batteries should be reliable and safe for permanent human implantation. Where appropriate, the construction of the battery should lend itself readily to remote recharging according to known and future methods. Finally, it would be advantageous if such batteries were amenable to inexpensive and simple manufacture without unduly compromising either the operating capabilities or the long-term reliability of the battery.

Batteries incorporating the construction of this invention will have these characteristics to greater and lesser extents and in different combinations according to the particular requirements of the uses for which those batteries are designed.

SUMMARY OF THE INVENTION

The invention provides electrical storage battery assemblies and related methods for assembling such batteries. Batteries incorporating the invention will frequently include electrode assemblies comprising positive and negative electrode sheets that are physically separated by a separator sheet. These sheets may be sandwiched together and wrapped around a central mandrel to provide a spiral sandwich electrode assembly.

In some embodiments the central mandrel will include spring arms that provide spring tension to hold the spiral sandwich electrode assembly under tension, helping to ensure uniformity in the electrode sheets, and thereby helping to ensure that the assembled battery will function reliably and predictably.

The battery's electrode assembly is housed inside a case. In preferred embodiments, the case includes a case housing open at two ends and covers closing the two openings after the electrode assembly has been installed inside the case housing.

The central mandrel of the electrode assembly may be placed into direct electrical contact with one of the electrode sheets and then connected to a first battery terminal that passes through the case. The connection between the central mandrel and the first battery terminal may be provided through an electrically conductive projecting member formed integral with or otherwise in electrical contact with the central mandrel. In a preferred embodiment, the projecting member includes a tab that is suitable for welding to the first battery terminal.

The other electrode, the one not placed into electrical contact with the first battery terminal, may be placed into electrical contact with the case. This electrical contact may be established, e.g., by welding an electrically conducting tab member between that electrode and the case housing. In some embodiments, a second battery terminal can be provided and placed in electrical contact with the case. The second battery terminal can be formed onto a fill plug, which can be installed into an opening in the case to seal the case after the battery assembly has been filled with an electrolyte fluid.

Where a projecting member is used to connect one of the electrodes to the first battery terminal, a first insulator may be positioned between the electrode assembly and the projecting member to guard against short circuits in the battery. A second insulator can be used between the projecting member and the case. Where the case is electrically connected to one of the electrodes, the other electrode in the electrode assembly should be electrically isolated from the case by a third insulator.

DESCRIPTION OF THE PREFERRED EMBODIMENTS

Figure 1:
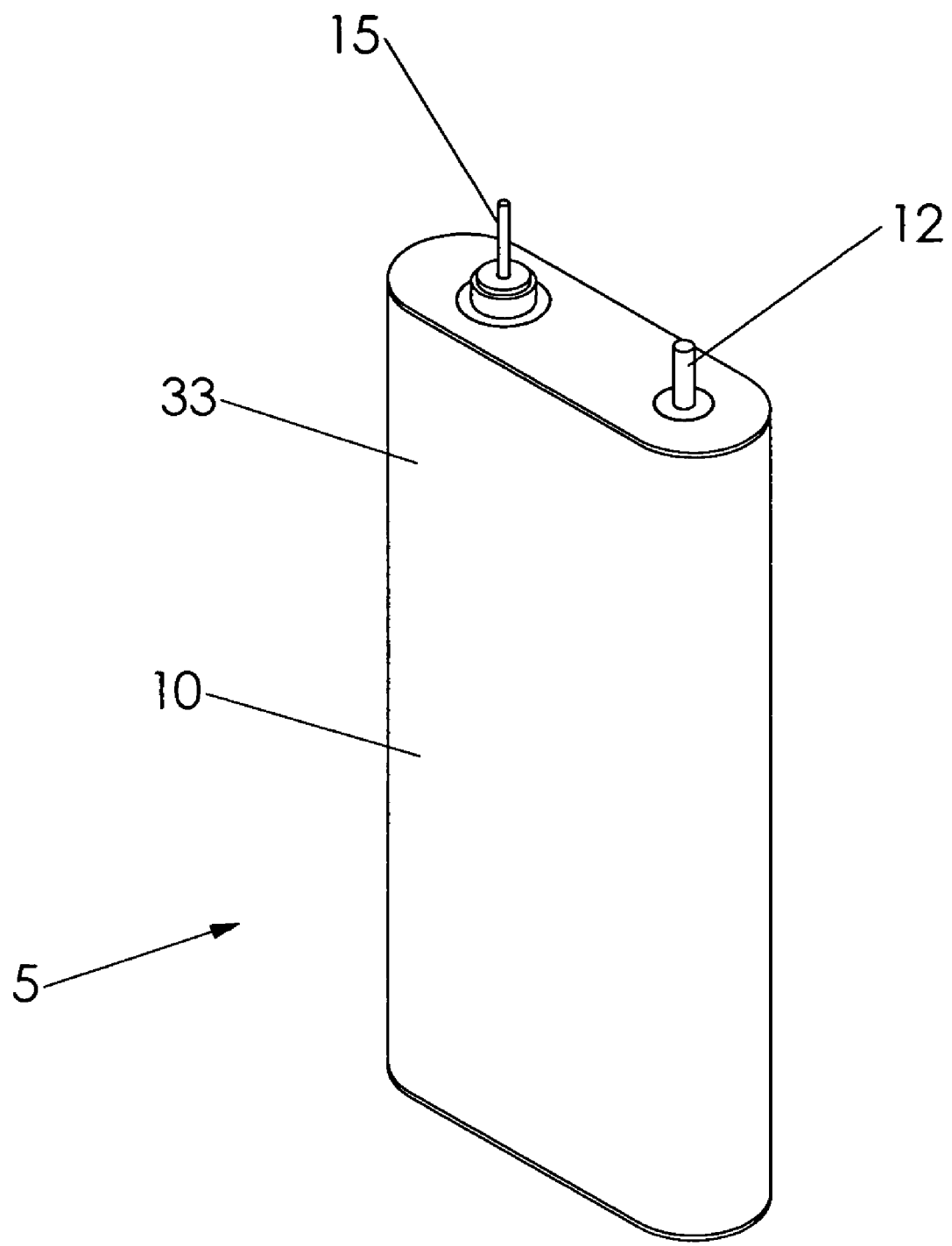
FIG. 1 shows a battery assembly according to the invention.

FIG. 1 depicts one embodiment of an electric storage battery 5 assembled in accordance with the invention. The battery is assembled inside a case 10 and includes a positive terminal 12 and a negative terminal 15.

Figure 2:
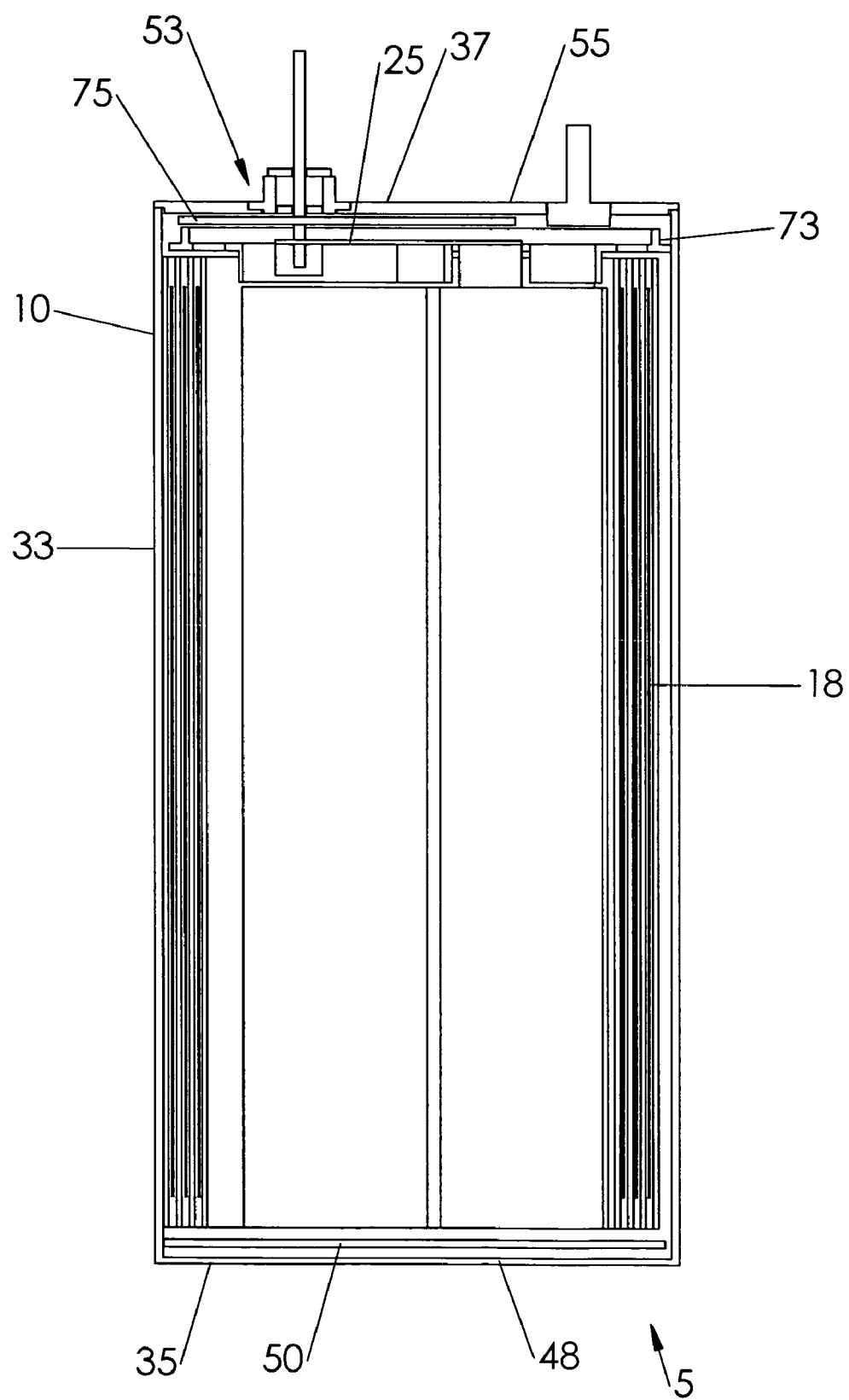
FIG. 2 is a side-section view of the battery shown in FIG. 1.

FIG. 2 is a side-section view of the battery 5 shown in FIG. 1. A spiral sandwich electrode assembly 18 is located inside the case 10. Workers in this art sometimes refer to this kind of electrode assembly as a "jellyroll" electrode assembly.

The electrode assembly in this battery comprises positive and negative electrode sheets sandwiched together with a separator sheet between them. The separator sheet has openings in it that allow an electrolyte to permeate between the positive and negative electrode sheets. The separator sheet thus physically separates the two electrode sheets while allowing electric current to flow between them. An electrode assembly may include several sheets of each type in a multiple-electrode sandwich. The preferred embodiment, however, includes only a single sheet of each type, sandwiched together and wrapped around a central mandrel. Each electrode is generally formed of a sheet of substrate coated with an active material.

Figure 3:
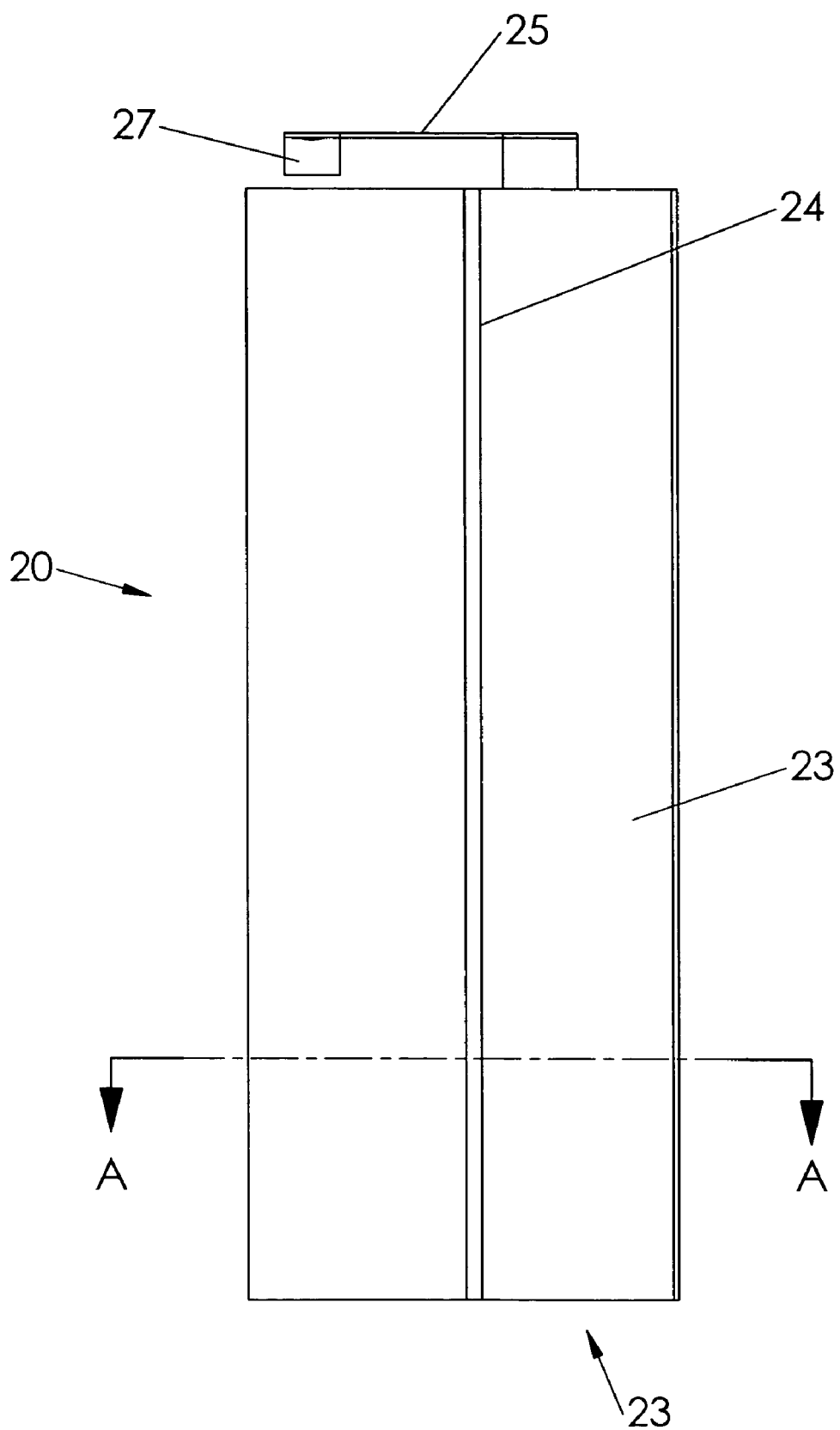
FIG. 3 is a side view of a mandrel that forms a part of the battery shown in FIGS. 1 and 2.
Figure 4:
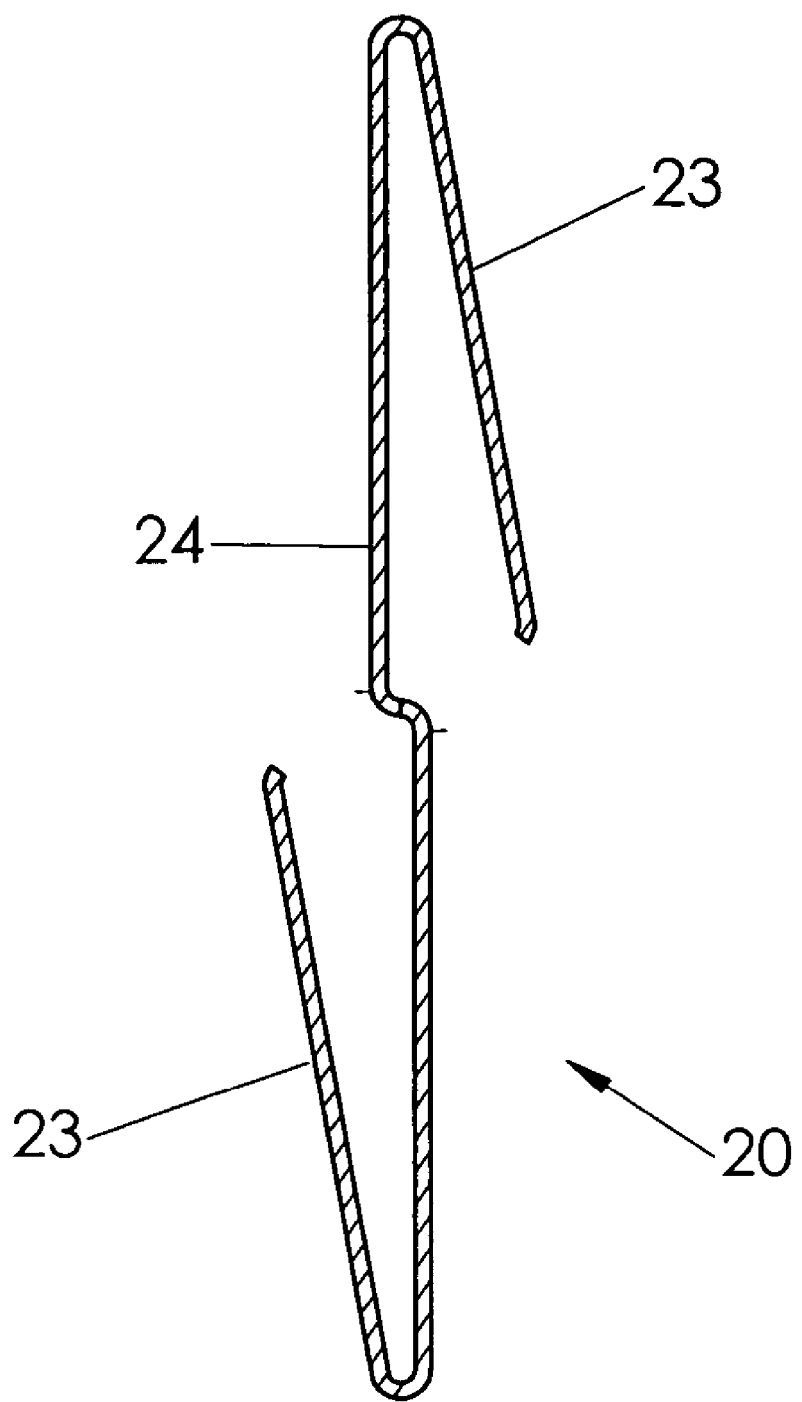
FIG. 4 is a top-section view of the mandrel shown in FIG. 3.

FIG. 3 is a side view of one embodiment of the mandrel 20. FIG. 4 is a top-section view through section lines A-A of FIG. 3, depicting the mandrel in its unloaded, pre-assembly condition. Referring especially to FIG. 4, the mandrel 20 includes two spring arms 23, one on each side of a central mandrel main body 24. The mandrel in this spring embodiment is formed preferably from Titanium CP grade 1 or 2 or a 300 series stainless steel. Note that the mandrel need not be a spring configuration but may be any configuration to act as a central support to the jellyroll.

Figure 5:
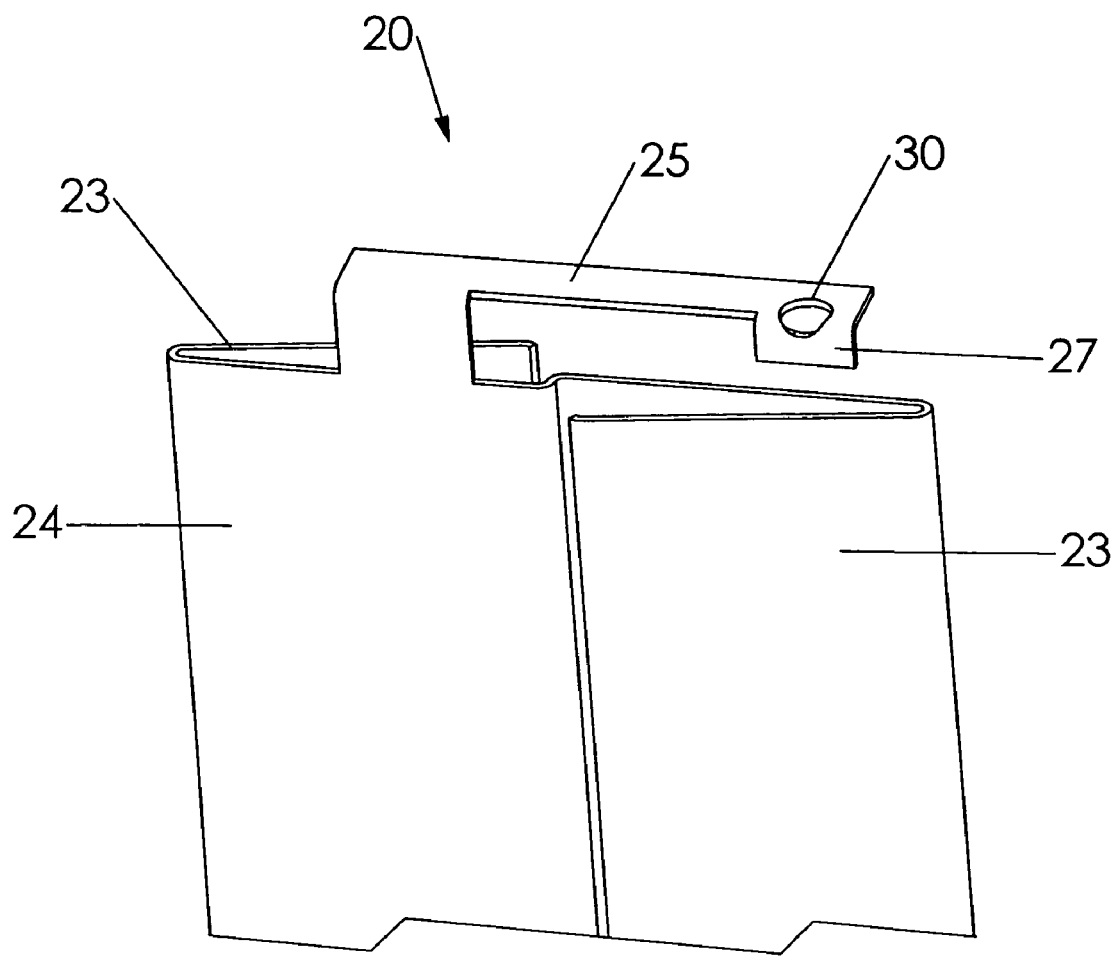
FIG. 5 illustrates the top end of the mandrel depicted in FIGS. 3 and 4.

FIG. 5 depicts the top end of the mandrel 20. The mandrel includes a projecting arm 25 at the top of the mandrel. The projecting arm includes an underside tab 27, and a connector opening 30 through the material of the projecting arm. The opening on the connecting arm will be used to connect the mandrel to an electrical terminal in the battery. This will be described in more detail below.

To assemble the battery, one first fits the mandrel 20 onto wrapping machinery (not shown). The wrapping machinery wraps the electrode sandwich sheet—comprising at least one each of a positive electrode sheet, a negative electrode sheet, and an intervening separator sheet—around the mandrel to form the wrapped spiral sandwich electrode jellyroll. The mandrel thus serves as a central support member for the spiral sandwich electrode member. The electrode sandwich should be wrapped onto the mandrel with the negative electrode sheet on the inner side in direct contact with the mandrel. The mandrel will eventually be connected to the negative terminal of the battery.

For the spring configuration of the mandrel 20, as the electrode sheet is wrapped onto the mandrel 20, the two spring arms 23 are held flat against the mandrel main body 24. Spring tension arises in the spring arms from the elasticity of the mandrel material. This spring tension helps to hold the flexible electrode sheet material taut as it is wrapped around the mandrel. This helps to ensure uniform and predictable wrapping, which is important to the proper and reliable functioning of the assembled battery. The spring arms continue to provide tension on the electrode and separator sheet materials during the life of the battery, keeping them in contact while they undergo expansion and contraction that occurs with cycling of the battery.

Figure 6:
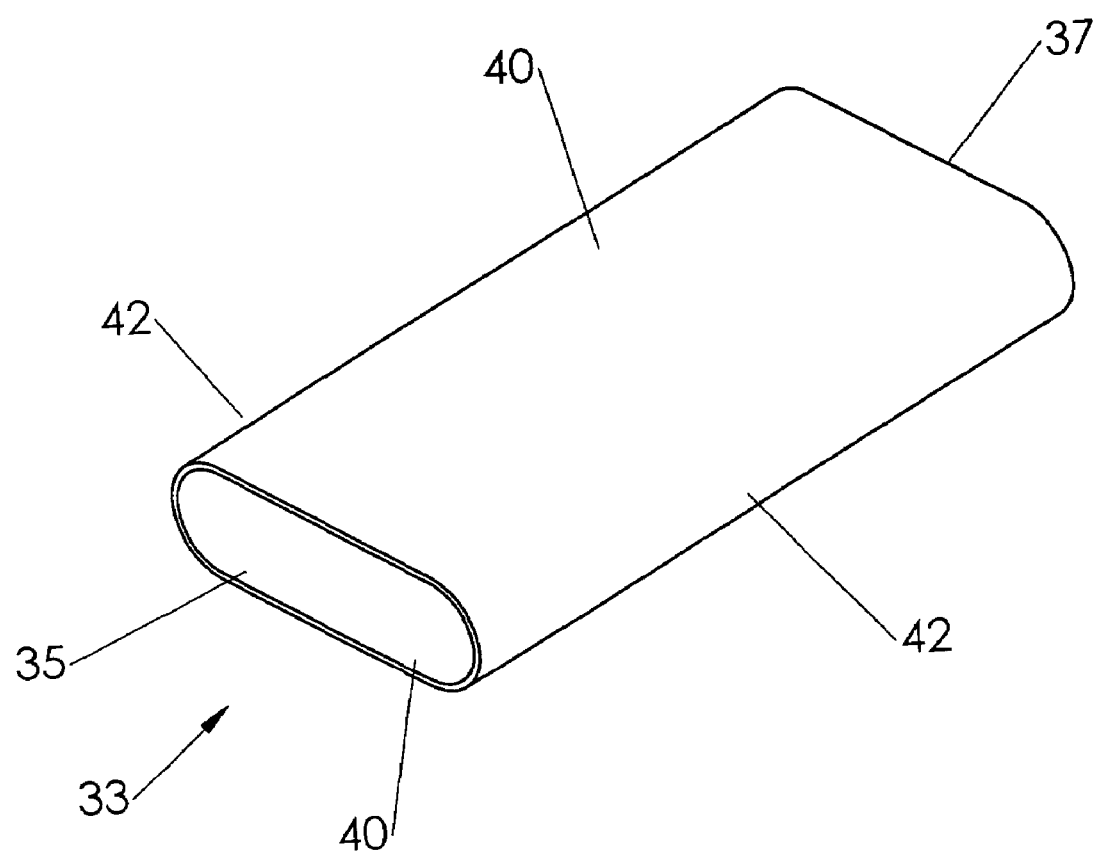
FIG. 6 shows a case housing that forms a part of the assembled battery.

The battery is assembled and contained inside a case 10 (see FIGS. 1 and 2). A major component of the case is a case housing 33, which is illustrated in FIG. 6. The case housing, preferably formed from Titanium 6-4, is hollow and open at first and second ends 35 and 37. The material of the case housing allows for efficient inductive remote recharging, as little energy is lost by conversion to heat within a housing of this material. The case may be produced by removing material from a block of Ti-6Al-4V to form an outer shape having two opposing ends, hollowing out the shaped block from one end partway through to the other end, then hollowing out the shaped block from the other end to form a through hole with the first hollowed out end. Machining or EDM may be used to form the outside shape as well as to hollow out the inside. This technique is especially useful when a noncylindrical battery case is desired.

The case housing includes planar walls 40, which are parallel to one another with rounded walls 42 serving as transition structure between the two planar walls. An internal volume is defined inside the case housing between the planar walls and the open first and second ends. Battery components are assembled inside this internal volume in the case housing. Note that while case housing 33 is described above as having parallel planar walls with rounded walls transitioning between them, the case housing is not limited to that shape, and may be cylindrical, cubic, or other shapes.

Figure 7:
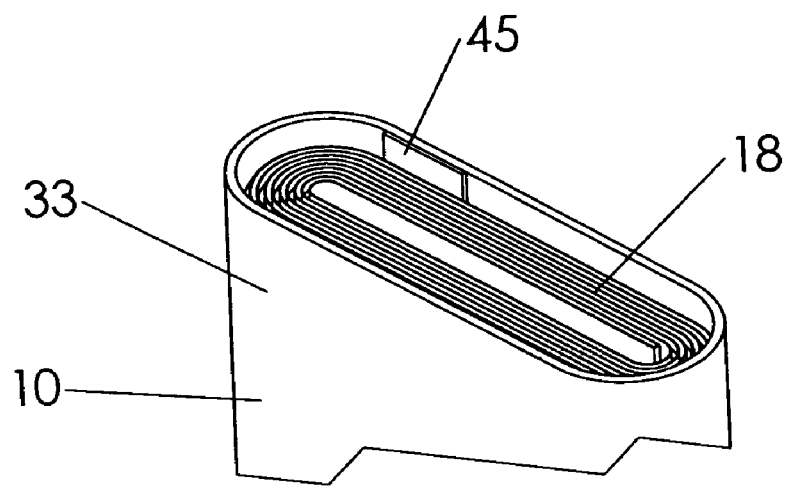
FIG. 7 shows a spiral electrode assembly installed inside the case housing of FIG. 6.
Figure 8:
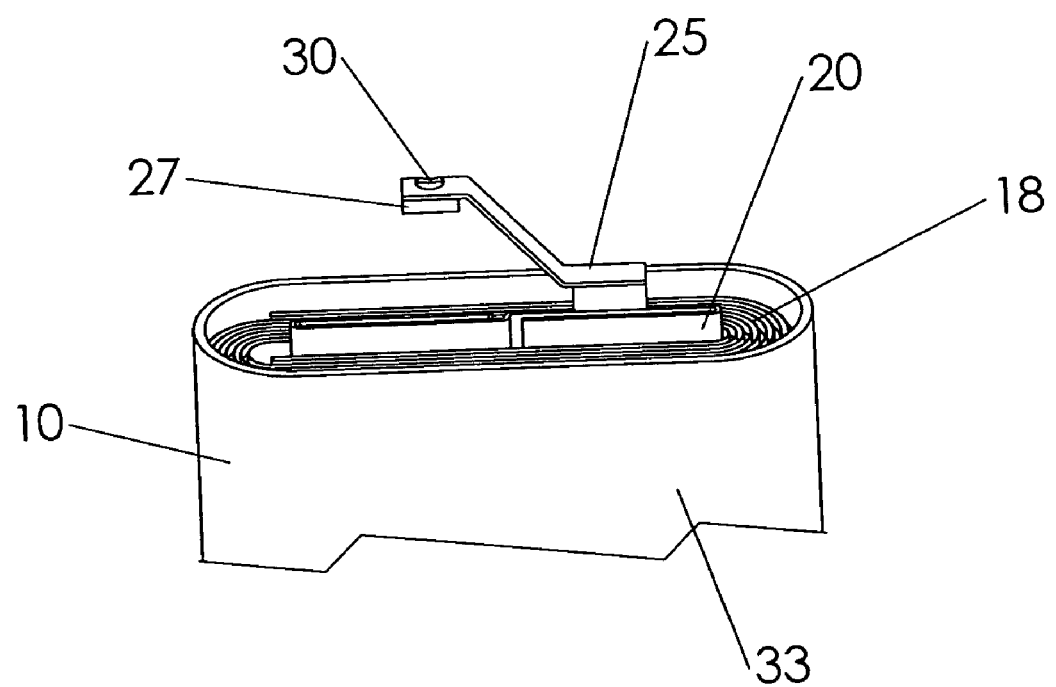
FIG. 8 depicts a top end of the mandrel of FIGS. 3-5, inside the spiral electrode and case housing of FIGS. 6 and 7.

FIG. 7 shows the spiral electrode assembly 18 inserted inside the case housing 33. Although the central mandrel 20 is omitted from FIG. 7 for clarity, it remains inside the tightly wrapped electrode assembly as indicated in FIG. 8. Omission of the mandrel from FIG. 7 allows for a clearer view of a tab 45. Aluminum is the preferred positive substrate. Because of the difference in resistivity and thickness between the aluminum substrate and the case, they cannot be easily resistance welded together. Laser welding the substrate to the case is also difficult due to space constraints. Tab 45 is provided to electrically and mechanically join the aluminum substrate to the Ti-6-4 case by welding one end to the positive electrode of the electrode assembly and the other end to the interior of the titanium case housing 33. The tab preferably is ultrasonically welded to the positive electrode prior to winding the electrode to create the jellyroll. Welding prior to winding the electrode obviates the need to ultrasonically weld in a confined space, which would be difficult. When the jellyroll is formed, the tab extends from it. The jellyroll is then inserted into the case and the tab is resistance welded to the case. The tab is made of a material that is corrosion resistant to positive potential, and is preferably the same material as the case to facilitate resistance welding to it. This is a convenient and reliable way to ensure secure electrical contact between the positive electrode and the (thus positively charged) battery case 10. Alternatively, tab 45 may be laser welded to the case, but this is a more expensive process than resistance welding.

FIG. 8 depicts the rolled spiral electrode assembly 18 inside the case housing 33, as in FIG. 7. FIG. 8, though, shows the projecting arm 25 of the mandrel 20 extended above the electrode assembly. A cover assembly will eventually be assembled onto the case housing to seal the case 10. This will be described in more detail below.

Referring again to FIG. 2, the case housing 33 is sealed at its first (bottom) end 35 by a case bottom 48. The case bottom is formed from Titanium 6-4, the same material as the case housing. The electrode assembly 18 is isolated from the case bottom by a bottom insulator 50, which preferably is formed from polypropylene or, alternatively, is formed from polyperfluoroalkoxyethylene (PFA).

Figure 9:
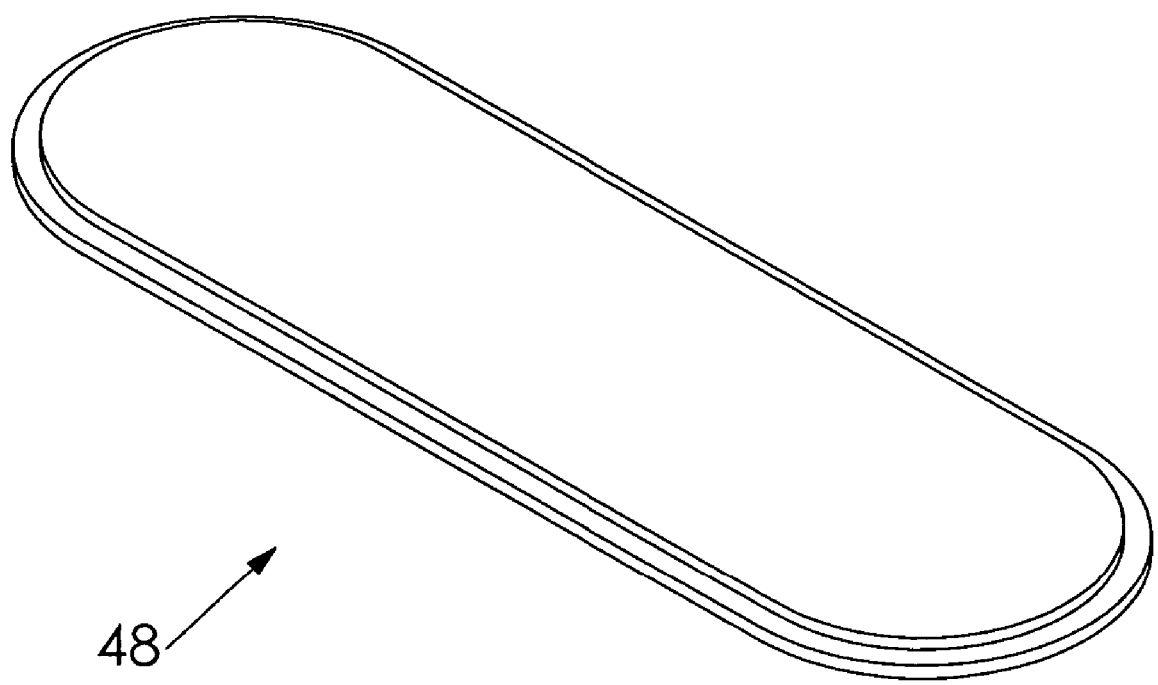
FIG. 9 shows a case bottom that closes one end of the case housing depicted in FIG. 6.
Figure 10:
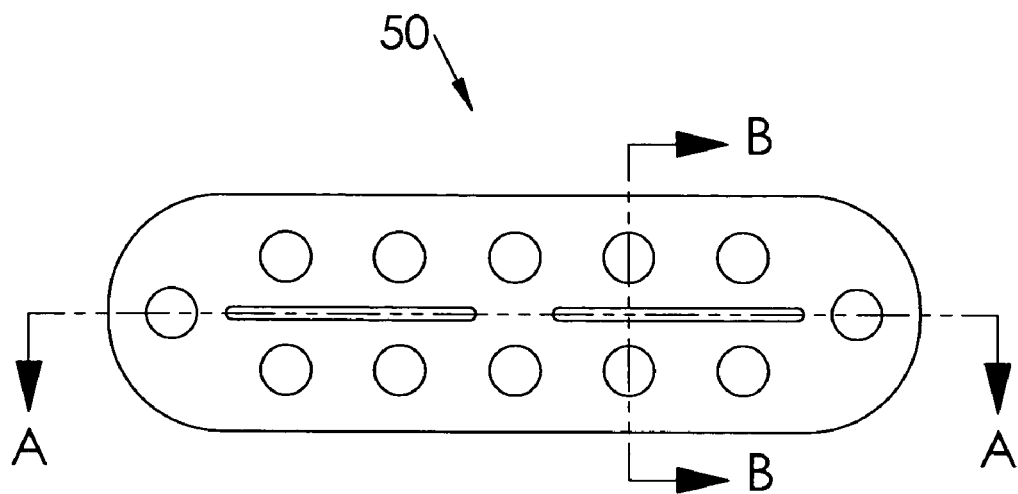
FIG. 10 is a top view of a bottom insulator that is positioned inside the assembled battery between the case bottom of FIG. 9 and the spiral electrode assembly.
Figure 11:
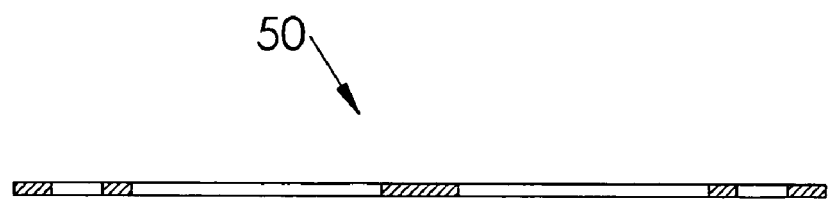
FIG. 11 is a side-section view of the bottom insulator shown in FIG. 10.
Figure 12:
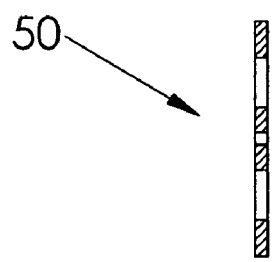
FIG. 12 is a second side-section view of the bottom insulator depicted in FIGS. 10 and 11.

A perspective view of the case bottom 48 is provided in FIG. 9. FIG. 10 is a top view of the bottom insulator 50. FIG. 11 is a side-section view of the bottom insulator 50 through section lines A-A of FIG. 10. FIG. 12 is a side-section view of the bottom insulator 50 through section lines B-B of FIG. 10.

Figure 13:
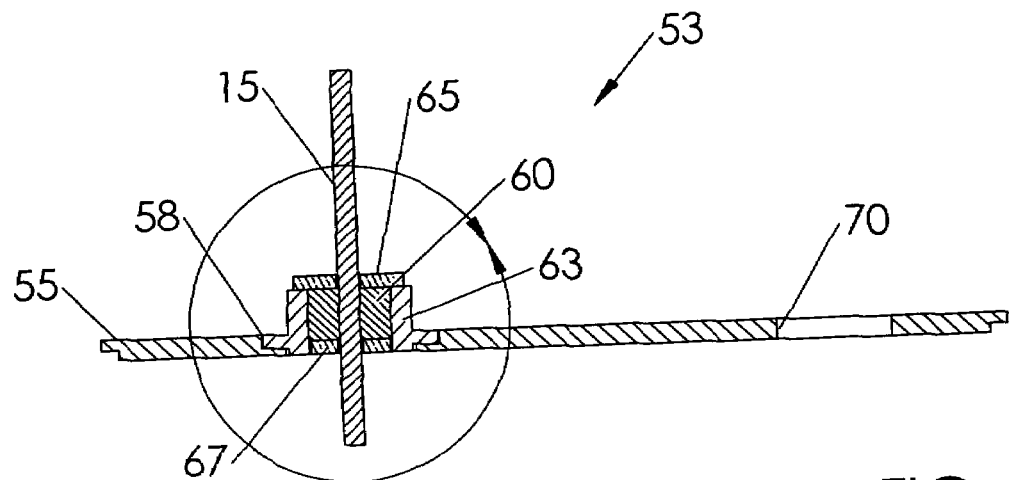
FIG. 13 is a side-section view of a cover assembly that closes off the top end of the housing case shown in FIG. 6.

Referring again to FIG. 2, the battery case 10 is sealed at its second (top) end 37 by a cover assembly 53. FIG. 13 is a side-section view of the cover assembly. As illustrated therein, the cover assembly comprises a case lid 55 with a negative terminal 15 passing through a first opening 58 in the case lid. The case lid is made of titanium 6-4, and in the assembled battery is in electrical contact with the positively charged case.

Figure 14:
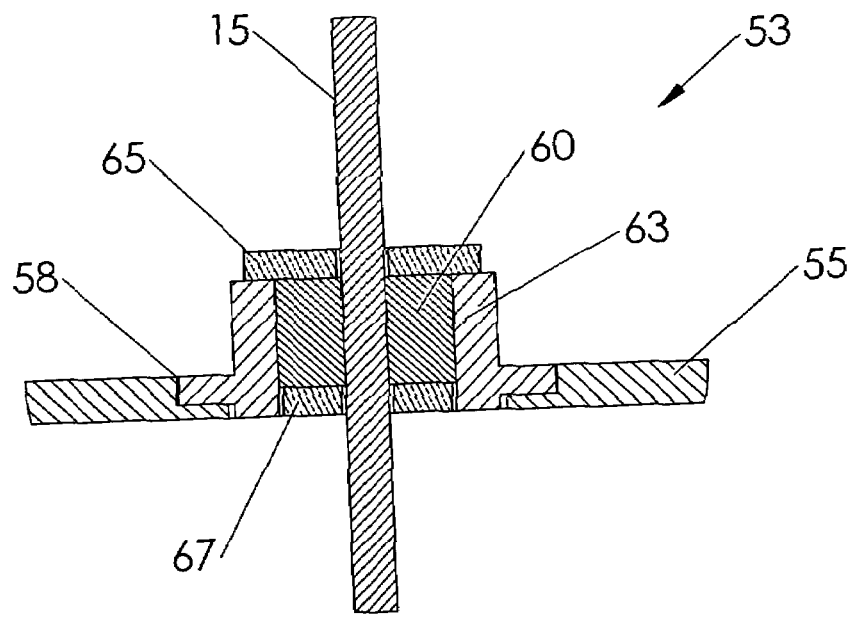
FIG. 14 is a detail view, in side-section, showing a portion of the cover assembly of FIG. 13.

FIG. 14 is a detail view, in side-section, of the region of the cover assembly 53 where the negative terminal 15 passes through the first opening 58 in the case lid 55. An insulative spacer 60 holds the negative terminal in place inside a ferrule 63. The negative terminal 15 preferably comprises a PtIr alloy and the ferrule 63 preferably is made from Ti-6-4. The insulative spacer 60 is electrically nonconductive and is preferably made from a glass such as CaBAl 12. A topside closure 65 and bottomside closure 67 keep the insulative spacer material from flowing when heated during assembly and are therefore preferably made from a high melt temperature insulative ceramic.

Figure 15:
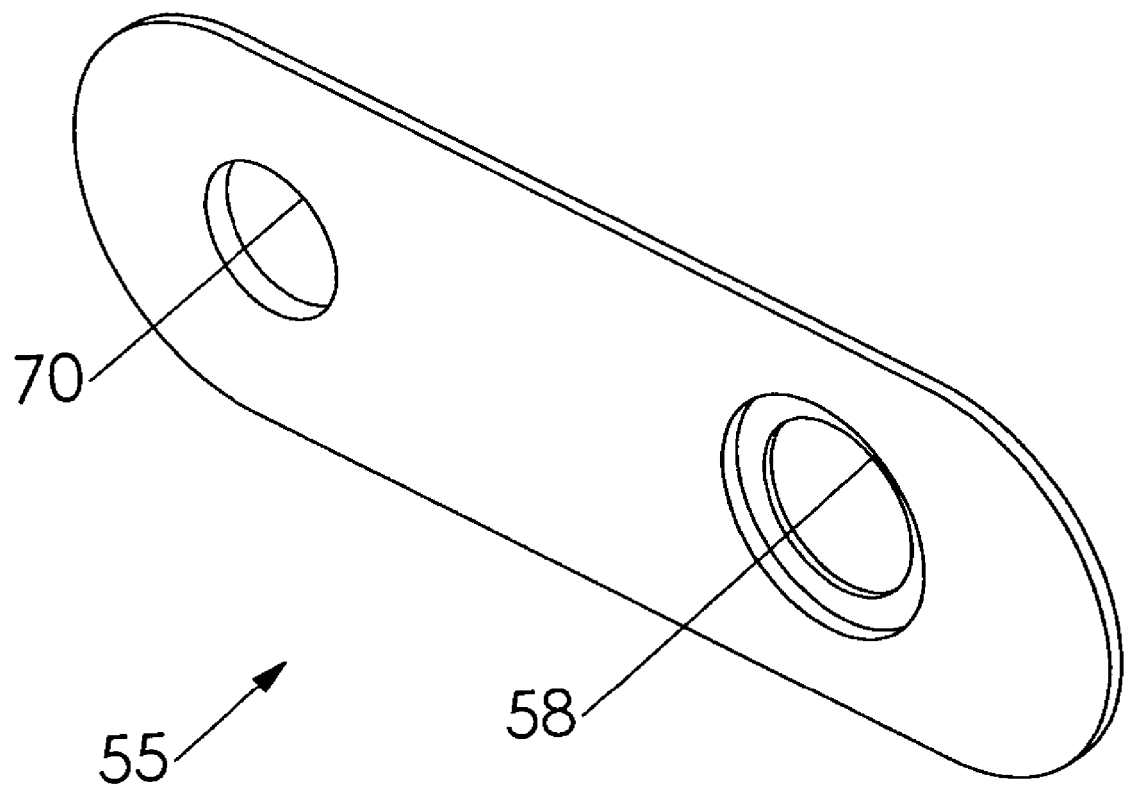
FIG. 15 depicts a case lid that forms a part of the cover assembly of FIGS. 13 and 14.

FIG. 15 is a perspective view showing the case lid 55, including the first case lid opening 58 and a second case lid opening 70. As indicated therein, the first case lid opening has a stepped profile sized to receive the stepped profile on the underside of the ferrule 63 (see FIG. 14). The second case lid opening serves as a fill hole through which electrolyte is later received into the battery assembly.

Figure 16:
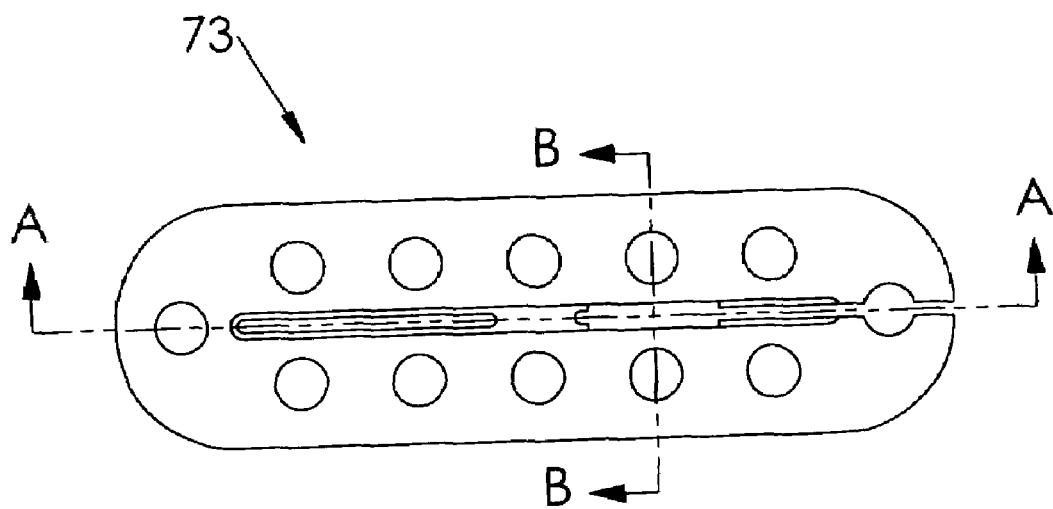
FIG. 16 is a top view of a top insulator that lies between the case lid of FIG. 15 and the spiral electrode assembly in the assembled battery.
Figure 17:
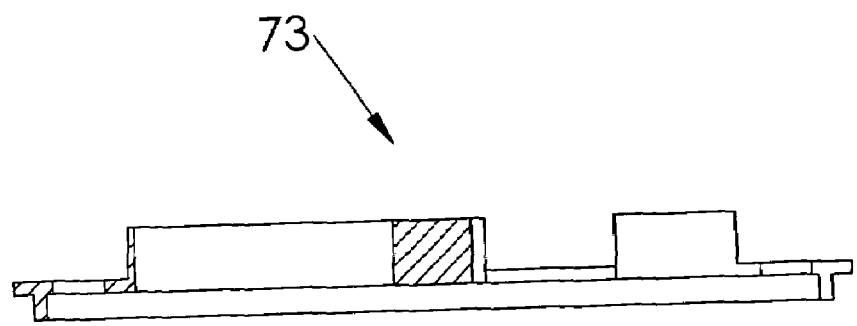
FIG. 17 is a side-section view of the top insulator shown in FIG. 16.
Figure 18:
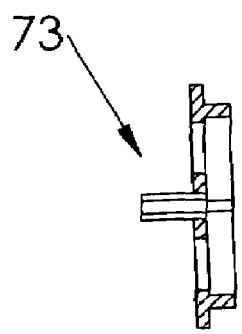
FIG. 18 is a second side-section view of the top insulator illustrated in FIGS. 16 and 17.

Referring again to FIG. 2, the rolled electrode assembly 18 is electrically isolated from the top cover assembly 53 by a top insulator 73, which preferably is polypropylene for its low cost, and a cover insulator 75, which preferably is formed from PFA to prevent melting during the laser weld of the cover to the case. Alternatively, insulators 73 and 75 both may be formed from electrically nonconductive polypropylene or PFA. FIG. 16 provides a top view of the top insulator 73. FIG. 17 is a section view through section lines A-A of FIG. 16. FIG. 18 is a section view through section lines B-B of FIG. 16.

Figure 19:
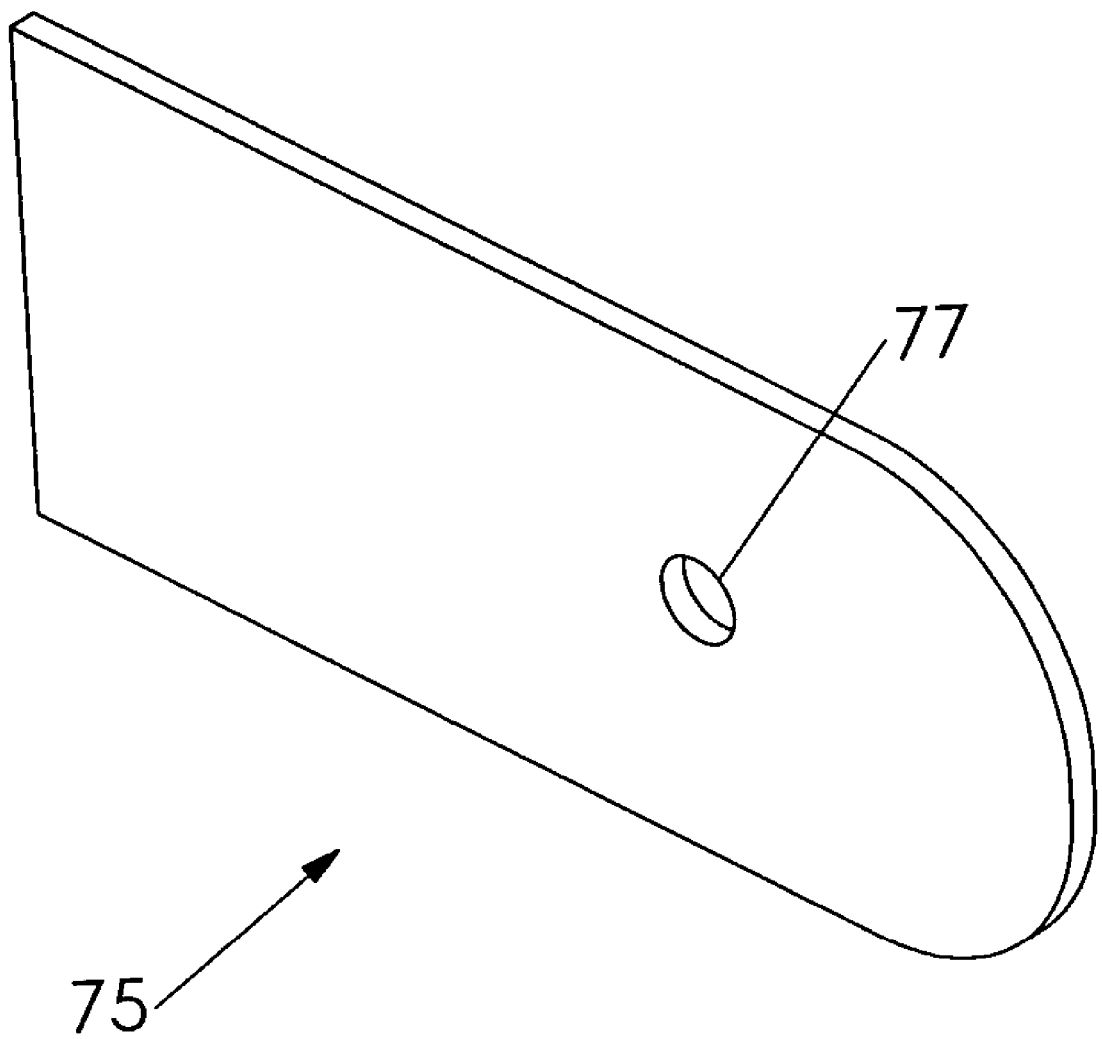
FIG. 19 illustrates a cover insulator that lies between the top insulator of FIGS. 16-18 and the case lid of FIG. 15 in the assembled battery.

A perspective view of the cover insulator 75 is provided in FIG. 19. The cover insulator includes a terminal opening 77, which will receive the negative terminal 15 (see FIG. 2). The cover insulator may optionally include a fill hole opening that aligns with the second case lid opening 70 in the case lid 55 (not shown).

Figure 20:
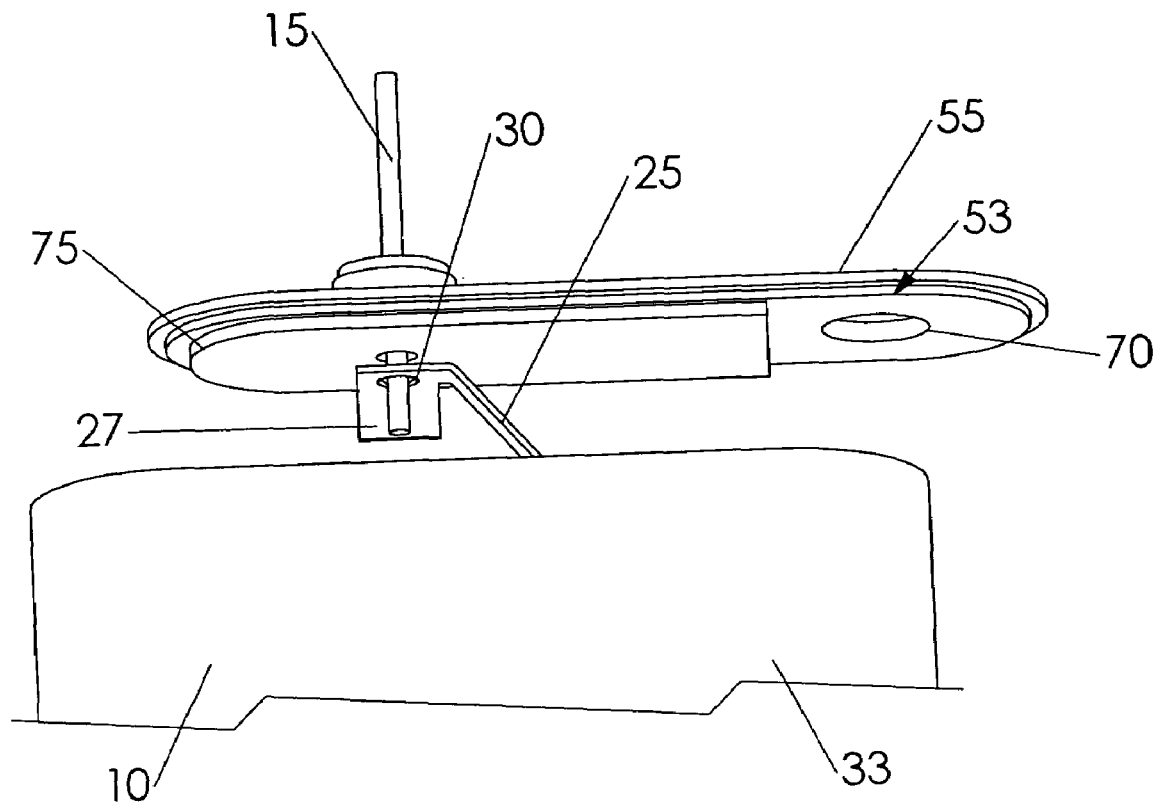
FIG. 20 shows the assembly of the cover assembly of FIG. 13 onto the top of the case housing of FIG. 6.

FIG. 20 illustrates the assembly of the cover assembly 53 onto the top of the case housing 33. With the top insulator 73 already in place below the rim of the case housing 33 (see FIG. 2), the bottom end of the negative terminal 15 is passed through the opening 30 in the projecting arm 25 of the mandrel 20. The underside tab 27 on the projecting arm is then welded to the bottom end of the negative terminal 15. The underside tab in this embodiment provides a convenient configuration for welding, as the tab projects away from and is clear of the structure of the projecting arm 25. Furthermore, because the projecting arm is preferably flexible, the projecting arm can be bent away from the electrode assembly for ease of welding. Laser welding and resistance welding are suitable methods to weld the tab to the bottom 27 of the negative terminal 15.

Although the projecting arm in the illustrated embodiment is formed integrally with the rest of the mandrel, other embodiments may include other projecting arms or other structure for connecting the central mandrel to one of the electrodes. Such alternative structures may be formed integrally with the central mandrel, or they may be connected to the mandrel by any means that provides a reliable electrical connection between the central mandrel and the battery terminal. The projecting arm 25 is flexible, but is preferably not excessively springy to avoid creating residual stress in the battery when the cover is closed.

When the cover assembly 53 is pressed down against the top of the case housing 33, the projecting arm 25 is compressed and sandwiched between the top insulator 73 and the cover insulator 75. The negatively charged projecting arm is thus electrically isolated from both the positive electrode of the rolled electrode assembly 18 (see FIG. 2) and the positively charged case lid 55. When the cover assembly is in place with the case lid pressed firmly against the case housing 33, the case lid can be joined, e.g., by laser welding, to the case housing to seal that part of the case 10. This assembly method produces a configuration that is reliable and requires a minimum of headspace in the battery. This design, with its three strategically placed insulators, is protected against internal shorts.

After the cover assembly 53 is sealed in place, the assembled battery 5 is filled with an appropriate electrolyte through the electrolyte fill hole provided by the second case lid opening 70. When sufficient electrolyte has been filled into the battery, the electrolyte fill hole is sealed by the introduction of a fill hole plug 82 into the second opening 70 in the case lid 55. The fill hole plug 82 preferably is slightly tapered for ease of insertion into opening 70.

Figure 21:
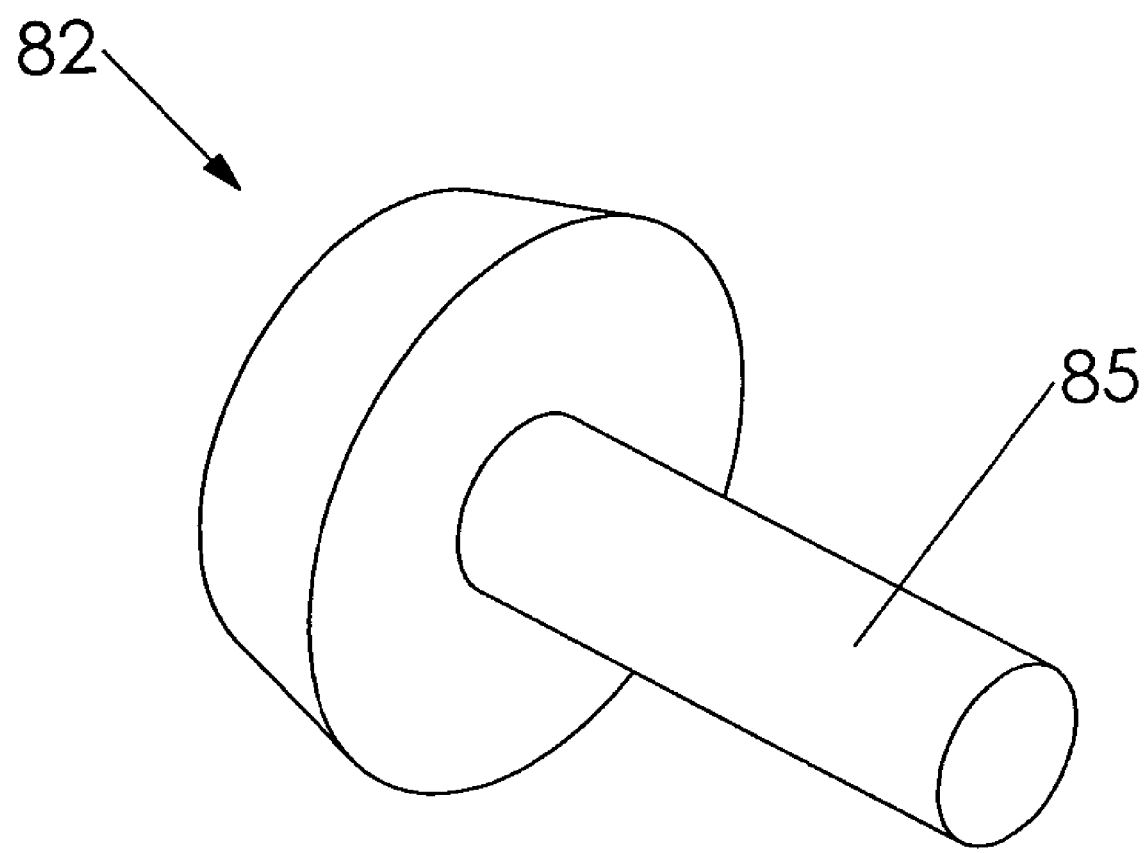
FIG. 21 depicts a fill plug that seals the case of the battery after the battery has been filled with electrolyte.

The fill hole plug, which is depicted in FIG. 21, is of the same material, titanium 6-4, as the case lid 55. The fill hole plug can be securely sealed into the second case lid opening 70, again, e.g., by laser welding. When the fill hole plug is secured in place, an upper projection 85 of the fill hole plug serves as a positive terminal pin 12 of the battery (see FIG. 2).

Specific embodiments of battery assemblies and related methods for manufacturing them have been described in considerable detail above. Those of skill in the art may devise additions, improvements, and modifications to these embodiments and methods. For example, the invention has been described for a configuration having a positive case and fill plug terminal, and a negative electrode coupled to the mandrel. The polarities of all of the components may be reversed, with appropriate changes to the materials, as would be clear to one skilled in the art. The scope of the invention is not limited to the specific embodiments described above. The scope of the invention should be judged instead by reference to the appended claims, along with the full scope of equivalents to which those claims are legally entitled.

What is claimed is:

1. A method of assembling a battery, comprising:
   filling a case through a fill-hole in a cover of a case, the case being configured to hold an electrode assembly having at least one positive electrode and at least one negative electrode; and
   plugging the fill-hole with a plug having a terminal extending from a top of a plug region,
   the fill-hole being plugged such that the plug region extends across the fill-hole and is positioned between an interior of the case and the terminal.

2. The method of claim 1, wherein the terminal has a narrower diameter than the top of the plug region.

3. The method of claim 2, wherein the plug region is tapered.

4. The method of claim 2, wherein the plug region is constructed of an electrically conducting material and the terminal is constructed of an electrically conducting material.

5. The method of claim 4, wherein the terminal and plug region are both constructed of the same material.

6. The method of claim 4, wherein the terminal and plug region are both constructed of the same material as the cover.

7. The method of claim 1, wherein the plug is constructed of a single material.

8. The method of claim 1, wherein plugging the fill-hole with the plug provides electrical communication between the cover and the terminal.

9. The method of claim 1, further comprising:
   providing electrical communication between the electrode assembly and the case, the case being in electrical communication with the cover, and plugging the fill-hole with the plug provides electrical communication between the cover and the terminal.

10. The method of claim 1, wherein one electrode member of the positive electrode and the negative electrode includes a tab extending from an arm, and further comprising:
    providing electrical communication between a second terminal and the tab.

11. The method of claim 1, wherein an interface between the terminal and the upper surface of the plug region is within a perimeter of the upper surface of the plug region.

12. A battery comprising:
    a cover attached to a case configured to hold an electrode assembly having at least one positive electrode and at least one negative electrode; and
    a plug positioned in a fill-hole in the cover, the fill-hole configured such that the case can be filled with an electrolyte through the fill-hole, the plug having a terminal extending from a top of a plug region, the plug region extending across the fill-hole and being positioned between an interior of the case and the terminal.

13. The battery of claim 12, wherein the terminal has a narrower diameter than the top of the plug region.

14. The battery of claim 13, wherein the plug region is tapered.

15. The battery of claim 13, wherein the plug region is constructed of an electrically conducting material and the terminal is constructed of an electrically conducting material.

16. The battery of claim 15, wherein the terminal and plug region are both constructed of the seine material.

17. The battery of claim 15, wherein the terminal and plug region are both constructed of the same material as the cover.

18. The battery of claim 12, wherein the plug is constructed of a single material.

19. The battery of claim 12, wherein the terminal is in electrical communication with the cover.

20. The battery of claim 19, wherein
    one electrode member of the positive electrode and the negative electrode includes a tab extending from an arm, and further comprising:
    a second terminal in electrical communication with the tab.

* * * * *